United States Patent [19]

Eibl et al.

[11] 4,388,232

[45] Jun. 14, 1983

[54] METHOD OF PRODUCING PLASMA FRACTIONS FREE OF SIDE-EFFECTS USING FAST-REACTING ANTITHROMBIN

[75] Inventors: Johann Eibl; Fritz Elsinger; Yendra Linnau, all of Vienna, Austria

[73] Assignee: Immuno Aktiengesellschaft für Chemisch Medizinische Produkte, Vienna, Austria

[21] Appl. No.: 375,044

[22] Filed: May 5, 1982

Related U.S. Application Data

[63] Continuation-in-part of Ser. No. 135,234, Mar. 31, 1980, abandoned.

[30] Foreign Application Priority Data

Apr. 19, 1979 [AT] Austria ................................ 2940/79

[51] Int. Cl.[3] .............................................. C07G 7/00
[52] U.S. Cl. ................................. 260/112 B; 424/101; 424/177
[58] Field of Search .................... 260/112 B; 424/101, 424/177

[56] References Cited

U.S. PATENT DOCUMENTS 3,803,115  4/1974  Fekete et al. .................... 260/112 B
4,137,223  1/1979  Shanbrom et al. .............. 260/112 B
4,203,891  5/1980  Rock ............................... 260/112 B

FOREIGN PATENT DOCUMENTS 2324717  5/1973  Fed. Rep. of Germany .
2184898  5/1973  France .
2001528  7/1978  United Kingdom .

OTHER PUBLICATIONS

R. D. Rosenberg, "The Function of Heparin," *Heparin Chemistry & Clinical Usage*, pp. 101–119 (1976).
Vox Sang. 36:281–293 (1979), Wicker Havseretial.
Thrombosis Research, vol. 61, pp. 287–294 (1975), Odegard et al.
"Preparation of Nonthrombogenic Prothrombin Complex", Thromb. Res. 1978, 12 (4), 571–582:. Chandra et al.
Kirk-Othmer, Encyclopedia of Chem. Technology pp. 556–583 (1948).
Kowalski et al., "Heparin and the Inactivation of Thrombin by Anti-Thrombin III," *Thrombosis Research* pp. 387–397 (1979).
Chem. Abstracts, vol. 84, Nr. 7, Feb. 16, 1976, Abstract No. 40350e, p. 188, Columbus, Ohio, U.S., J. S. Rosenberg et al., "Inhibition of Human Factor IXa by Human Antithrombin", J. Biol. Chem. 1975, 250 (23) 8883–3.
Chem. Abstracts, vol. 89, Nr. 7, Aug. 14, 1978, Abstract No. 55381t p. 213, Columbus, Ohio, U.S., S. Chandra et al., "Large Scale".

*Primary Examiner*—Howard E. Schain
*Attorney, Agent, or Firm*—Brumbaugh, Graves, Donohue & Raymond

[57] ABSTRACT

In a method of producing plasma fractions free of side-effects by purification and step-wise enrichment of plasma proteins in the presence of calcium-binding anticoagulants, also fast reactive (avid) antithrombin is present, wherein a concentration of the fast reacting (avid) antithrombin of 0.05 to 50 units per ml of the respective solution is maintained during all fractionation process steps.

12 Claims, No Drawings

METHOD OF PRODUCING PLASMA FRACTIONS FREE OF SIDE-EFFECTS USING FAST-REACTING ANTITHROMBIN

This application is a continuation-in-part application of Ser. No. 135,234 filed Mar. 31, 1980, now abandoned.

The invention relates to a method of producing plasma fractions free of side effects from plasma or plasma crude fractions, by purification and stepwise enrichment of plasma proteins, such as by filtration, cryoprecipitation, precipitation, adsorption, ultrafiltration, centrifugation and lyophilization in the presence of calcium-binding anticoagulants, such as citrate ions.

More particularly, the invention relates to a method of producing side-effect-free coagulation-factor preparations, immune globulin preparations and inhibitor preparations, such as C1-esterase inhibitors.

When storing and processing human and animal plasma, a number of enzymes become active, leading i.a. to changes, such as degradation or activation, of high-molecular plasma proteins. These changes may lead to the formation of byproducts, which, due to their biologic activity, cause undesired side effects in vivo and in vitro.

When producing concentrates of highly effective coagulation factors and other plasma proteins with biologic activity, the danger of enzymatically caused protein changes, which may lead to undesired side reactions, is particularly great.

It has already been known, when recovering the prothrombin complex from plasma, to add antithrombin III to the elution solution for the purpose of inactivation of thrombin (Sudhish Chandra and Milan Wickerhauser, Large Scale Preparation of Nonthrombogenic Prothrombin Complex, Thrombosis Research, 12, 571 (1978)).

Furthermore it is known to add heparin to the end product when producing the prothrombin complex, in order to prevent an activation of prothrombin (New England Journal of Medicine, 280, 291 (1969)).

According to other authors (Jean-Pierre Soulier and Marion Steinbuch, Zeitschr. Ges. Inn. Med. 20, Suppl., 311, (1965)) heparin has a stabilizing effect on the prothrombin complex. Also D. Ménaché and H. Roberts have suggested, according to Thromb. Diath. haemorrh. (Stuttgart) 33, 645 (1975), the addition of heparin to prothrombin-complex preparations.

Finally, the addition of heparin during the fractionation of factor-VIII-preparations in order to increase the yield of factor VIII is known from German Offenlegungsschrift No. 2,324,717.

Although both the addition of antithrombin and the addition of heparin have thus been suggested by several authors for the preparation of coagulation-factor preparations, no one has so far succeeded in obtaining side-effect-free plasma fractions of human or animal origin, in particular side-effect-free coagulation-factor preparations with uniform effectiveness—in a reliable and repeatable manner—and there has continued the demand for achieving this object.

It has now been found that it is not antithrombin or heparin as such which are essential and effective in the prevention of undesired biologic changes in the plasma or plasma fractions, but what matters is the presence of fast reacting (avid) antithrombin.

The expression "fast reacting (avid) antithrombin" as used herein refers to the well-known phenomenon that the inhibition effect of thrombin by antithrombin (AT) is dramatically accelerated by the presence of heparin. It is, for instance, pointed out in an article by Kowalski, S. and Finlay, F. H. in Thrombosis Research 14, 387–397, 1979, that the formation of the inactive thrombin-antithrombin complex is accelerated by heparin. It is postulated that AT binds with heparin and undergoes a change which increases its ability to react with thrombin.

This effect is also reported in an article by Robert D. Rosenberg, "The Function of Heparin", published in Heparin Chemistry and Clinical Usage edited by Kakkar et al., 1976 Academic Press, pp. 101–119, 10.

Thus, the term "fast reacting (avid) antithrombin" is used herein to describe the complex of antithrombin and heparin or a heparin equivalent which is reactive in inhibiting thrombin and other serine proteases, i.e., "fast reacting (avid) antithrombin" is an antithrombin which is formed by adding a cofactor such as heparin to antithrombin.

The terms "heparinoids" and "heparin equivalents" as used herein are substances that have the same effect as heparin in that they accelerate the thrombin-inhibiting reaction of antithrombin, "heparinoids" being sulfated polysaccharides, e.g. dextrane sulfates sulfopolyglucans, glycosaminoglycans, sulfated pectins.

Accordingly, the method according to the invention consists in that the purification and enrichment of the plasma proteins, in particular of coagulation factors, of immune globulin and of inhibitors, such as C1-esterase inhibitors, is being carried out in the presence of fast reacting (avid) antithrombin.

It has also been found that it does not suffice to simply add a stabilizing agent to the end product or in a more or less arbitrary manner at any intermediate step of the fractionation-process, which is inherent in the prior art mentioned, but the concentration of the fast reacting (avid) antithrombin has to be kept at or above a certain measure during the entire fractionation-process. Accordingly, it falls within the method of the invention that during all the steps of the fractionation-process a concentration of the fast reacting (avid) antithrombin of 0.05 to 50, preferably of 0.5 to 50 units of the same per ml of the respective solution, is maintained.

One unit of the avid antithrombin, abbreviated by 1 $AT_{av}$-U, is defined as that amount of $AT_{av}$ which inhibits one NIH-(National Institute of Health)-unit of thrombin in one minute. For the purpose of determination, 2 NIH-units of thrombin are incubated at 37° C. with the sample to be tested for $AT_{av}$. After one minute a thrombin-sensitive, chromogenic substrate on peptide basis (e.g. substrate S-2238 of Kabi) is added to the incubation mixture and the amount of thrombin that has not been inhibited is determined photometrically.

The method of the invention can be realized in various ways. An advantageous embodiment of the invention consists in that the fast reacting (avid) antithrombin is formed in situ by the addition of inhibitor-cofactors. As inhibitor cofactors heparin or heparinoids can be used.

A particularly preferred and important embodiment of the method according to the invention consists in that the fast reacting (avid) antithrombin, preferably in the form of the antithrombin-III-cofactor-complex, is preformed, and is added as the preformed antithrombin-cofactor-complex in portions during the individual fractionation steps.

The method according to the invention will be explained in more detail by way of the following examples:

EXAMPLE 1

Preparation of a factor-VII-concentrate: 1 l of fresh-frozen human citrated plasma was thawed at 0° to 2° C., the resulting cryoprecipitate being separated by centrifugation. In the supernatant (cryo-supernatant) containing factor VII, 7 units of fast reacting (avid) antithrombin per ml (7 $AT_{av}$-U/ml) were formed in situ by the addition of 0.5 International Units (I.U.) of heparin per ml. After 15 minutes, 0.5 g of DEAE-Sephadex (diethylaminoethyl-group containing cross-linked dextrane) were added to the cryo-supernatant on stirring: after further stirring for 30 minutes at a temperature of no more than 5° C. the DEAE-Sephadex was separated by sedimentation or centrifugation. In the DEAE-Sephadex-supernatant, 7 $AT_{av}$-U/ml were again formed in situ by the addition of 0.5 I.U. of heparin/ml. After 15 minutes, 7 ml of a 5% suspension of aluminum hydroxide were added to the DEAE-Sephadex-supernatant on stirring; after further 15 minutes of stirring at a temperature of below 5° C. the aluminum hydroxide was separated by centrifugation. The aluminum hydroxide, containing factor VII in adsorbed form, now was treated with 100 ml (1/10 of the original plasma volume) of a washing solution containing 4 g/l of trisodium citrate.2-H$_2$O and 7 g/l of sodium chloride. Furthermore, 10 units/ml of preformed avid antithrombin (10 $AT_{av}$-U/ml) were added to the solution. The preformation of the avid antithrombin, i.e. of the antithrombin-III-cofactor-complex, took place outside the fractionation-process proper, by the combination of a solution of purified antithrombin III and a heparin solution, wherein, in the resulting solution, 0.5 units of purified antithrombin III and 0.5 I.U. of heparin per ml were contained. After 10 minutes of stirring at 5° C., the washed aluminum hydroxide was separated by centrifugation and factor VII was eluted at an increased ionic strength. For this purpose, the aluminum hydroxide was treated with 50 ml (1/20 of the original plasma volume) of an elution solution containing 45 g/l of secondary sodium phosphate (Na$_2$HPO$_4$.12H$_2$O) and 4 g/l of trisodium citrate.2H$_2$O as well as 10 units/ml of avid antithrombin (10 $AT_{av}$-U/ml) preformed in this solution. The preformation of the antithrombin-III-cofactor-complex was performed as described above. The pH of the elution solution was adjusted to 8.5 by an acid phosphate solution (78 g/l of NaH$_2$PO$_4$.2H$_2$O). After 20 minutes of stirring at 5° C. the aluminum hydroxide was separated by centrifugation and discarded. The eluate containing factor VII was adjusted to a pH of 7.5 with the acid phosphate solution and then dialyzed at 5° C. against demineralized water.

The dialyzed eluate was subjected to a first lyophilization; the bulk thus obtained was tested for the factor-VII-content as well as for the presence of activated coagulation factors by means of the "NAPTT"-(NON-ACTIVATED PARTIAL THROMBOPLASTIN-TIME)-test described in the following, and for activated factor VII (factor VIIa), which is not detected by the NAPTT-test.

NAPTT-test for the presence of activated coagulation factors:

(a) Reagents (a$_1$) Normal human citrated plasma, recovered only by means of plastic material equipment.

(a$_2$) Partial thromboplastin (phospholipid): "Tachostyptan" (Hormon Chemie, Munich) at a ratio of 1:200 diluted in "Tris" (tris-hydroxymethyl-aminomethane)/NaCl buffer.

(a$_3$) Buffer (as diluent for test samples and for phospholipid):

0.06 m "Tris"—7.26 g/l 0.09 m sodium chloride—5.27 g/l the pH was adjusted to 7.5 with 1 n hydrochloric acid.

(a$_4$) Calcium chloride: 0.025 m (m/40 CaCl$_2$).

The CaCl$_2$-solution was maintained at 37° C. during the test period.

The test sample and its dilutions as well as the citrated plasma (a$_1$) were stored in an ice bath during the test.

(b) Test method:

From the sample to be tested 10 geometric dilutions (1:2, 1:4 to 1:1,024) were prepared in plastic tubes on using "Tris"/NaCl-buffer.

These samples, together with a "blank value" (the buffer being used as sample), were tested in double determinations according to the following procedure (the "blank value" being determined at the beginning and at the end of the test period):

0.1 ml normal human citrated plasma 0.1 ml partial thromboplastin 0.1 ml sample

Incubation for one minute at 37° C.

0.1 ml m/40 CaCl$_2$

The time from the addition of calcium chloride to the clot formation was measured (tilting of the test tubes in the water bath of 37° C. or by using an automatic coagulometer).

If the undiluted sample or the first dilutions cause prolonged coagulation times relative to the "blank value", that amount of protamin sulfate has to be added to the sample which reduces the prolonged coagulation times to the lowest value possible.

(c) Interpretation of the test results:

The sample to be tested is free of activated coagulation factors ("non-activated"), if the coagulation times after the addition of the sample or its dilutions are not shorter than the shortest coagulation time of the "blank values" determined prior and after the test period (tolerance limit: 10–20 seconds, according to the error limit of the method; blank value: at least 200 seconds).

Test for the presence of activated factor VII (factor VIIa):

Principle of the test:

Factor VIIa can be inhibited by incubation with antithrombin III (AT III) and heparin in the cold; native, i.e. non-activated factor VII is stable under these conditions. The decrease of the factor-VII-activity of a sample after incubation with factor-VII-deficient plasma (AT III-source) and heparin compared to the factor-VII-activity of the same sample after incubation with a buffer (control), is a measure for the amount of factor VIIa present in the sample.

Test mixture (in plastic tubes):

1.0 ml test sample (dilution with buffer, to 10 units of factor VII per ml)

0.1 ml heparin (dilution with buffer, to 100 International Units of heparin per ml)

0.9 ml factor-VII-deficient plasma (AT III-source) control mixture (in plastic tubes):

1.0 ml test sample (10 units of factor VII per ml)

1.0 ml buffer (0.7% sodium chloride, 0.7% sodium citrate)

Both mixtures are stored over night in the refrigerator. On the next day, the factor-VII-activity of both mixtures is determined by means of a usual coagulation test on using factor-VII-deficient plasma.

Interpretation of the test result:

The decrease or inhibition of the factor-VII-activity of the sample in the test mixture relative to the control mixture is proportional to the factor-VIIa-content of the sample.

The calculation is carried out according to the following formula:

% Inhibition =

$$\left(1 - \frac{\text{Factor-VII-activity test mixture}}{\text{Factor-VII-activity control mixture}}\right) \times 100$$

0% Inhibition: the sample contains only non-activated factor VII.
100% Inhibition: the sample contains only activated factor VII (factor VIIa).

The tests carried out with the end product of Example 1 have shown an absence of activated coagulation factors. The bulk material was dissolved, mixed with sodium citrate and sodium chloride, sterilized by filtration, filled into final containers under sterile conditions, and finally lyophilized.

EXAMPLE 2

Comparative Experiment)

In this experiment a factor-VII-concentrate was prepared substantially according to the method described in Example 1, however with the variation of omitting the in-situ-formation of avid antithrombin in the cryo-supernatant as well as the in-situ-formation in the DEAE-Sephadex-supernatant, a slight amount of avid antithrombin (0.4 $AT_{av}$-U/ml) yet being present in a natural concentration.

No preformed avid antithrombin was added to the washing solution and to the elution solution. The NAPTT-test and the VIIa-test were positive, i.e. the end product contained activated coagulation factors. The comparison of the properties of the products of Example 1 and those of Example 2 is to be seen numerically in the following Table 1.

a 3% Al(OH)$_3$-suspension were added to the cryoprecipitate solution, the mixture was stirred for 30 minutes at room temperature and Al(OH)$_3$ was separated by cetrifugation.

To the supernatant further preformed avid antithrombin, prepared by mixing of 37 ml of human plasma and 74 I.U. of heparin, was added in order to make up for part of the avid antithrombin adsorbed at Al(OH)$_3$ and to further maintain its concentration in the solution at 6.0 $AT_{av}$-U/ml. In the next step 75 ml of a 53% ethanol solution were added in order to reach a concentration of 7% ethanol, thus precipitating part of the inert (non-factor-VIII-active) proteins. These proteins are separated and discarded. 39 ml of ethanol were added to the supernatant, a concentration of 10% ethanol in the solution thus being reached. The temperature was lowered to −2° C., the principal amount of the factor-VIII-containing fraction thus precipitating. This fraction was separated and dissolved in 150 ml of a 0.5% sodium chloride solution having a content of 0.2% citrate and 1.0% glycine. Also in this step, preformed avid antithrombin (27 ml human plasma and 54 I.U. of heparin) was added to the sodium chloride solution in order to keep the concentration constant at 6.0 $AT_{av}$-U/ml. The solution was filtered through a membrane filter down to a pore diameter of 0.2 μm, the factor-VIII-concentrate was filled into final containers and lyophilized.

The factor-VIII-concentrate was examined for the presence of activated coagulation factors, as described in Examples 1 and 2. The result was negative, i.e. it was free of activated coagulation factors.

EXAMPLE 4

Preparation of factor-VIII-concentrate by means of avid antithrombin preformed from purified antithrombin III and heparin.

10.8 l of fresh-frozen human citrated plasma were thawed at 0° to 2° C. The resulting cryoprecipitate in an amount of 100 g was centrifuged and dissolved in 400 ml of a 0.2% citrate buffer at a pH of 7.5 and a temperature of 37° C., after preformed avid antithrombin had been added to the citrate solution. The preformation was carried out by the admixture of a solution of 73.5 units of purified antithrombin III and 147 I.U. of heparin, the cryoprecipitate solution thus containing 6.0 $AT_{av}$-U/ml. 19.6 ml of a 3% Al(OH)$_3$-suspension were added to the cryoprecipitate solution, the mixture was stirred for 30 minutes at room temperature, and Al-

TABLE 1

| | Avid antithrombin units per ml ($AT_{av}$—U/ml) in | | | | Activation of the end products | |
|---|---|---|---|---|---|---|
| | Cryo-supernatant | DEAE-Seph.-supernatant | Washing solution | Elution solution | Activated coagulation factors (NAPTT)-test | Factor VIIa % Inhibition |
| Example 1 | 7 | 7 | 10 | 10 | non-activated | 0% |
| Example 2 | 0.4 | 0.4 | 0 | 0 | activated | 54% |

EXAMPLE 3

Preparation of Factor-VIII-concentrate by means of avid antithrombin preformed from plasma and heparin.

10.8 l of fresh-frozen human citrated plasma were thawed at 0° to 2° C. The resulting cryoprecipitate in an amount of 100 g was centrifuged and dissolved in 400 ml of a 0.2% citrate buffer at a pH of 7.5 and a temperature of 37° C., after preformed avid antithrombin had been added to the citrate solution. The preformation was effected by the admixture of a solution of 73.5 ml of human plasma and 147 I.U. of heparin, the cryoprecipitate solution thus containing 6.0 $AT_{av}$-U/ml. 19.6 ml of (OH)$_3$ was separated by centrifugation.

To the supernatant further preformed avid antithrombin, prepared by mixing 37 units of purified antithrombin III and 74 I.U. of heparin, was added in order to make up for part of the avid antithrombin adsorbed at Al(OH)$_3$ and to further maintain its concentration in the solution at 6.0 $AT_{av}$-U/ml. In the next step, 75 ml of a 53% ethanol solution were added in order to reach a concentration of 7% ethanol, thus precipitating part of the inert (non-factor-VIII-active) proteins. These proteins were separated and discarded. 39 ml of ethanol were added to the supernatant, a concentration of 10% ethanol in the solution thus being reached. The temperature was lowered to −2° C., the principal amount of the factor-VIII-containing fraction thus precipitating. This fraction was separated and dissolved in 150 ml of a 0.5% sodium chloride solution having a content of 0.2% citrate and 1.0% glycine. Also in this step, preformed avid antithrombin (27 units of purified antithrombin III and 54 I.U. of heparin) was added to the sodium chloride solution in order to maintain the concentration constant at 6.0 $AT_{av}$-U/ml. The solution was filtered through a membrane filter down to a pore diameter of 0.2 μm, the factor-VIII-concentrate was filled into final containers and lyophilized.

The factor-VIII-concentrate was examined for the presence of activated coagulation factors, as described in Examples 1 and 2. The result was negative, i.e. it was free of activated coagulation factors.

EXAMPLE 5

Preparation of factor-VIII-concentrate by means of avid antithrombin preformed from plasma and heparinoid.

10.8 l of fresh-frozen human citrated plasma were thawed at 0° to 2° C. The resulting cryoprecipitate in an amount of 100 g was centrifuged and dissolved in 400 ml of a 0.2% citrate buffer at a pH of 7.5 and a temperature of 37° C., after preformed avid antithrombin had been added to the citrate solution. The preformation was carried out by admixing a solution of 73.5 ml of human plasma and 1,470 units of Eleparon ® (heparinoid: mucopoly-saccharide polysulfuric acid ester), the cryoprecipitate solution thus containing 1.5 $AT_{av}$-U/ml. 19.6 ml of a 3% Al(OH)₃-suspension were added to the cryoprecipitate solution, the mixture was stirred for 30 minutes at room temperature, and Al(OH)₃ was separated by centrifugation.

To the supernatant further preformed avid antithrombin, prepared by mixing 37 ml of human plasma and 740 units of Eleparon ®, was added in order to make up for part of the avid antithrombin adsorbed at Al(OH)₃ and to further maintain its concentration in the solution at 1.5 $AT_{av}$-U/ml. In the next step, 75 ml of a 53% ethanol solution were added in order to reach a concentration of 7% ethanol, thus precipitating part of the inert (non-factor-VIII-active) proteins. These proteins were separated and discarded. 39 ml of ethanol were added to the supernatant, a concentration of 10% ethanol in the solution thus being reached. The temperature was lowered to −2° C., the principal amount of the factor-VIII-containing fraction thus precipitating. This fraction was separated and dissolved in 150 ml of a 0.5% sodium chloride solution having a content of 0.2% citrate and 1.0% glycine. Also in this step, preformed avid antithrombin (27 ml of human plasma and 540 units of Eleparon ®, was added to the sodium chloride solution in order to maintain the concentration constant at 1.5 $AT_{av}$-U/ml. The solution was filtered through a membrane filter down to a pore diameter of 0.2 μm, the factor-VIII-concentrate was filled into final containers and lyophilized.

The factor-VIII-concentrate was examined for the presence of activated coagulation factors, as described in Examples 1 and 2. The result was negative, i.e. it was free of activated coagulation factors.

EXAMPLE 6

Preparation of factor-VIII-concentrate by means of avid antithrombin preformed from purified antithrombin III and heparinoid.

10.8 l of fresh-frozen human citrated plasma were thawed at 0° to 2° C. The resulting cryoprecipitate in an amount of 100 g was centrifuged and dissolved in 400 ml of a 0.2% citrate buffer at a pH of 7.5 and a temperature of 37° C., after preformed avid antithrombin had been added to the citrate solution. The preformation was carried out by admixing a solution of 73.5 units of purified antithrombin III and 1,470 units of Eleparon ®, the cryoprecipitate solution thus containing 1.5 $AT_{av}$-U/ml. 19.6 ml of a 3% Al(OH)₃-suspension were added to the cryoprecipitate solution, the mixture was stirred for 30 minutes at room temperature, and Al(OH)₃ was separated by centrifugation.

To the supernatant further preformed avid antithrombin, prepared by mixing 37 units of purified antithrombin III and 740 units of Eleparon ®, was added in order to make up for part of the avid antithrombin adsorbed at Al(OH)₃ and to further maintain its concentration in the solution at 1.5 $AT_{av}$-U/ml. In the next step, 75 ml of a 53% ethanol solution were added in order to reach a concentration of 7% ethanol, thus precipitating part of the inert (non-factor-VIII-active) proteins. These proteins were separated and discarded. 39 ml of ethanol were added to the supernatant, thus reaching a concentration of 10% ethanol in the solution. The temperature was lowered to −2° C., the principal amount of the factor-VIII-containing fraction precipitating. This fraction was separated and dissolved in 150 ml of a 0.5% sodium chloride solution having a content of 0.2% citrate and 1.0% glycine. Also in this step, preformed avid antithrombin (27 units of purified antithrombin III and 540 units of Eleparon ®) was added to the sodium chloride solution in order to maintain the concentration constant at 1.5 $AT_{av}$-U/ml. The solution was filtered through membrane filters down to a pore diameter of 0.2 μm, the factor-VIII-concentrate was filled into final containers and lyophilized.

The factor-VIII-concentrate was examined for the presence of activated coagulation factors, as described in Examples 1 and 2. The result was negative, i.e. it was free of activated coagulation factors.

EXAMPLE 7

Preparation of factor-VIII-concentrate without avid antithrombin, however with the addition of heparin to a plasma fraction (comparative experiment).

10.8 l of fresh-frozen human citrated plasma were thawed at 0° to 2° C. The resulting cryoprecipitate in an amount of 100 g was centrifuged and dissolved in 400 ml of a 0.2% citrate buffer at a pH of 7.5 and a temperature of 37° C. 19.6 ml of a 3% Al(OH)₃-suspension were added to the cryoprecipitate solution, the mixture was stirred for 30 minutes at room temperature and Al(OH)₃ was separated by centrifugation.

To the supernatant 75 ml of a 53% ethanol solution were added in order to reach a concentration of 7% ethanol, thus precipitating part of the inert (non-factor-VIII-active) proteins. These proteins were separated and discarded. 39 ml of ethanol were added to the supernatant, a concentration of 10% ethanol in the solution thus being reached. The temperature was lowered to −2° C., the principal amount of the factor-VIII-containing fraction thus precipitating. This fraction was separated and dissolved in 150 ml of a 0.5% sodium chloride solution having a content of 0.2% citrate and 1.0% glycine. 54 I.U. of heparin were added to the sodium chloride solution. The solution was filtered through membrane filters down to a pore diameter of 0.2 μm, the factor-VIII-concentrate was filled into final containers and lyophilized.

The preparation was examined for the presence of activated coagulating factors, as described above. It was shown that the addition of heparin to the last fraction of the fractionation-process was not sufficient for preventing activations. The activation test was positive, i.e. activated coagulation factors were present, and the preparation thus had to be rejected.

EXAMPLE 8

Preparation of factor-VIII-concentrate without avid antithrombin and without the addition of heparin (comparative experiment):

10.8 l of fresh-frozen human citrated plasma were thawed at 0° to 2° C. The resulting cryoprecipitate in an amount of 100 g was centrifuged and dissolved in 400 ml of a 0.2% citrate buffer at a pH of 7.5 and a temperature of 37° C. 19.6 ml of a 3% Al(OH)$_3$-suspension were added to the cryoprecipitate solution, the mixture was stirred for 30 minutes at room temperature, and Al(OH)$_3$ was separated by centrifugation.

To the supernatant 75 ml of a 53% ethanol solution were added in order to reach a concentration of 7% ethanol, thus precipitating part of the inert (non-factor-VIII-active) proteins. These proteins were separated and discarded. 39 ml of ethanol were added to the supernatant, a concentration of 10% ethanol in the solution thus being reached. The temperature was lowered to −2° C., the principal amount of the factor-VIII-containing fraction precipitating. This fraction was separated and dissolved in 150 ml of a 0.5% sodium chloride solution having a content of 0.2% citrate and 1.0% glycine. The solution was filtered through membrane filters down to a pore diameter of 0.2 μm, the factor-VIII-concentrate was filled into final containers and lyophilized.

The preparation was examined for the presence of activated blood coagulation factors, as described above. The activation test was positive, i.e. such activated factors were present and the preparation had to be rejected.

Although, in the foregoing, the method according to the invention has been explained in detail for the production of factor VII and factor VIII concentrates, it is in the same manner suitable and advantageous also for the preparation of factor IX or prothrombin complex concentrates, respectively.

EXAMPLE 9

Preparation of a purified immune globulin fraction.

To 208 l of human blood plasma containing antithrombin III heparin was added in an amount of 6 I.U. per ml. to form the complex compound in a concentration of 18.5 AT$_{av}$-U/ml. Thereto ethanol was added at a pH of 7.2 and a temperature of −2° C. to give a concentration of 8% with a precipitate forming.

After separation of the precipitate the ethanol concentration was raised to 25%. The thus forming precipitate was extracted in a phosphate acetate buffer and 12% ethanol was added thereto at a pH of 5.2 and a temperature of −2° C. At this stage the solution contained 0.5 U AT$_{av}$-U/ml. The precipitate was discarded and the ethanol concentration of the supernatant was raised to 25% at a pH of 7.2 and a temperature of −8° C.

The pasty immune globulin fraction obtained was further fractionated in accordance with the invention as follows:

100 g immune globulin paste were dissolved in saline, i.e. a 0.9% sodium chloride solution, in the presence of 300 units of antithrombin III and 600 units of heparin to give a solution that contains 6.0 AT$_{av}$-U/ml, and thereafter dialyzed. At 20° C. 170 g/l ammonium sulfate were added, after separation of the precipitate the ammonium sulfate concentration of the supernatant was raised to 275 g/l to precipitate the purified immune globulin fraction. The latter was dissolved in saline, dialyzed and sterile-filtered after concentration by ultrafiltration.

EXAMPLE 10

(Comparative Experiment)

Preparation of an immune globulin fraction without the addition of antithrombin III/heparin-complex.

To 208 l of human blood ethanol was added at a pH of 7.2 and a temperature of −2° C. to give a concentration of 8% with a precipitate forming.

After separation of the precipitate the ethanol concentration was raised to 25%. The thus forming precipitate was extracted in a phosphate acetate buffer and 12% ethanol was added thereto at a pH of 5.2 and a temperature of −2° C. The precipitate was discarded and the ethanol concentration of the supernatant was raised to 25% at a pH of 7.2 and a temperature of −8° C.

The pasty immune globulin fraction was further fractionated as follows:

100 g immune globulin paste were dissolved in saline and thereafter dialyzed. At 20° C. 170 g/l ammonium sulfate were added, after separation of the precipitate the ammonium sulfate concentration of the supernatant was raised to 275 g/l to precipitate the purified immune globulin fraction. The latter was dissolved in saline, dialyzed and sterile-filtered after concentration by ultrafiltration.

EXAMPLE 11

Preparation of C1-esterase inhibitor.

250 g DEAE-Sephadex were stirred into 100 l of human blood plasma. The Sephadex-gel was separated and the C1-esterase inhibitor was eluted with the help of 10% NaCl which contained 3,000 units of antithrombin III and 6,000 units of heparin, so that the solution contained 6.0 AT$_{av}$-U/ml.

The C1-esterase inhibitor is further purified from impurities as follows:

To the eluate 22% polyethylene glycol 4,000 was added, the precipitate obtained was separated and discarded. By the addition of 28% polyethylene glycol the C1-esterase inhibitor was precipitated and separated. It was subjected to a further purification step. The precipitate was dissolved in saline containing 1,250 units of antithrombin III and 2,500 units of heparin, so that the solution contained 6.0 AT$_{av}$-U/ml. The impurities were precipitated with the help of 310 g ammonium sulfate per liter, separated and discarded. The purified C1-esterase inhibitor was precipitated by the addition of 405 g/l ammonium sulfate from the supernatant, collected, dissolved in saline, dialyzed and sterile-filtered.

EXAMPLE 12

(Comparative Experiment)

Example 11 was repeated, yet without the addition of the antithrombin III/heparin-complex.

The effect of biologically active substances is frequently tested on the ileum of the guinea pig. For this purpose, male SPF (specific pathogene free) guinea pigs (Dunkin-Hartley) having a body weight of 350 g are killed and 2 cm long ileum pieces are used. The ileum piece is put into a temperature controlled bath, which contains a tyrode buffer, having the following composition: 0.8% NaCl, 0.02% KCl, 0.02% $CaCl_2.2H_2O$, 0.01% $MgCl_2.6H_2O$, 0.1% $NaHCO_3$, 0.005% $NaH_2PO_4$, 0.1% glucose. By means of a force transducer the contractions caused by biologically active substances are transmitted to a recorder and recorded there.

The immune globulin preparation as obtained in accordance with Example 9, when tested on the ileum of a quinea pig as describes above, showed no contraction, while the preparation according to Example 10 above exhibited a very strong effect of contraction.

The $LD_{50}$-test serves for determining the toxicity of a preparation. $LD_{50}$ is the dose at which 50% of the animals die under experimental conditions. The preparation is intravenously injected in at least three dosages into ten NMRI (Navy Marine Research Institute) mice each, having a minimum body weight of 20 g. After an observation time of 7 days the living animals per dosage group are counted. The $LD_{50}$ is calculated in accordance with Wilson and Worcester, Proc. Nat. Acad. Sci. U.S.A. 29, 114 (1943).

Intravenous injection at maximum doses of the immune globulin preparations according to Examples 9 and 10 exhibited the following immediate effect on mice: The immune globulin preparation according to Example 9 was excellently tolerated, no animals died. With the immune globulin preparation according to Example 10 30% of the animals died.

The $LD_{50}$-effect was as follows: The C1-esterase-inhibitor preparation in accordance with Example 11 was excellently tolerated: $>>5,300$ units per kg body weight (maximum injectable amount C1-esterase-inhibitor). The tests with the preparation according to Example 12 resulted in $>3,250-<4,900$ units per kg body weight.

What we claim is:

1. A method of producing plasma fractions free of side-effects, by purification and step-wise enrichment of plasma proteins, by a technique selected from the group consisting of filtration, cryoprecipitation, precipitation, adsorption, ultrafiltration, centrifugation and lyophilization, in the presence of calcium-binding anticoagulants, which method comprises the purification and enrichment of the plasma proteins, in the presence of fast reacting (avid) antithrombin, while maintaining a concentration of the fast reacting (avid) antithrombin of 0.05 to 50 units per ml of the respective solution during all fractionation-process steps.

2. A method as set forth in claim 1, wherein a concentration of the fast reacting (avid) antithrombin of 0.5 to 50 units of the same per ml of the respective solution is maintained.

3. A method as set forth in claim 1, wherein fast reacting (avid) antithrombin is formed in situ by adding inhibitor-cofactors.

4. A method as set forth in claim 3, wherein heparin is added as inhibitor-cofactor.

5. A method as set forth in claim 3, wherein heparinoids are added as inhibitor-cofactors.

6. A method as set forth in claim 1, comprising the steps of preforming fast reacting (avid) antithrombin so as to obtain a preformed antithrombin-cofactor complex, and adding said preformed antithrombin-cofactor complex in portions during the individual fractionation-process steps.

7. A method as set forth in claim 6, wherein said preformed antithrombin-cofactor complex is an antithrombin-III-cofactor complex.

8. A method as set forth in claim 1, wherein the calcium-binding anticoagulants are citrate ions.

9. A method as set forth in claim 1, wherein the plasma fractions are coagulation-factors obtained from plasma.

10. A method as set forth in claim 1, wherein the plasma fractions are immune globulin fractions obtained from plasma.

11. A method as set forth in claim 1, wherein the plasma fractions are C1-esterase inhibitors.

12. A method as set forth in claim 9 wherein the coagulation-factors are selected from the group consisting of factor-VIII-containing concentrates and factor-VIII-containing concentrates.

* * * * *

UNITED STATES PATENT AND TRADEMARK OFFICE
CERTIFICATE OF CORRECTION

PATENT NO. : 4,388,232
DATED : June 14, 1983
INVENTOR(S) : Eibl et al.

It is certified that error appears in the above—identified patent and that said Letters Patent is hereby corrected as shown below:

First page, 2nd col., delete lines 7-9 and in line 21, following "Scale" insert --Preparation of Nonthrombogenic Prothrombin Complex," Thromb. Res. 1978, 12(4), 571-582:--. Col. 4, line 30, "m/40" should read --$m/40$--. Col. 5, line 33, "Comparative" should read --(Comparative--. Col. 11, line 21, "quinea" should read --guinea--. Col. 12, line 47, "factor-VIII-containing" should read --factor-VII-containing--.

Signed and Sealed this

Twenty-seventh Day of September 1983

[SEAL]

Attest:

GERALD J. MOSSINGHOFF

Attesting Officer   Commissioner of Patents and Trademarks